United States Patent [19]
King

[11] Patent Number: 5,637,494
[45] Date of Patent: Jun. 10, 1997

[54] STABILIZED CULTURES OF MICROORGANISMS

[75] Inventor: Andrew B. King, North Yorkshire, United Kingdom

[73] Assignee: Ecosyl Products Ltd., Billingham, United Kingdom

[21] Appl. No.: 239,843

[22] PCT Filed: Jan. 28, 1991

[86] PCT No.: PCT/GB91/00116
§ 371 Date: Sep. 29, 1992
§ 102(e) Date: Sep. 29, 1992

[87] PCT Pub. No.: WO91/11509
PCT Pub. Date: Aug. 8, 1991

Related U.S. Application Data

[63] Continuation of Ser. No. 862,764, Sep. 29, 1992, abandoned.

[30] Foreign Application Priority Data

Jan. 29, 1990 [GB] United Kingdom ............ 9002003

[51] Int. Cl.$^6$ .............. A01N 63/00; C12N 1/00; C12N 1/04; C12N 1/20
[52] U.S. Cl. .............. 435/252.1; 424/93.45; 435/243; 435/259.9; 435/260
[58] Field of Search .............. 435/243, 252.1, 435/252.9, 260; 424/93.45

[56] References Cited

U.S. PATENT DOCUMENTS

| | | | |
|---|---|---|---|
| 3,897,307 | 7/1975 | Porubcan et al. | 435/252.9 |
| 4,304,867 | 12/1981 | Kahan et al. | 435/253 |
| 4,345,032 | 8/1982 | Hata | 435/253 |
| 4,368,330 | 1/1983 | Andrews | 549/315 |
| 4,927,763 | 5/1990 | Sudoma et al. | 435/252.9 |

FOREIGN PATENT DOCUMENTS

| | | |
|---|---|---|
| 384621 | 12/1987 | Austria . |
| 1584694 | 5/1977 | United Kingdom . |

OTHER PUBLICATIONS

Merck Index, 11th edition, #5009, p. 809.

*Primary Examiner*—David M. Naff
*Assistant Examiner*—Deborah Ware
*Attorney, Agent, or Firm*—Cushman Darby & Cushman IP Group Pillsbury Madison & Sutro LLP

[57] ABSTRACT

Cultures of microorganisms, particularly in freeze dried form, include an ascorbic acid antioxidant and a monocarboxylic α-amino acid each of which are present at a mass fraction of 0.05 to 0.3. The acid acts as a potentiator for the antioxidant. The cultures are more stable for extended storage, particularly at relatively high temperatures, than unstabilized cultures. Further, additional components include a carbohydrate in an amount of 25 to 45 weight percent, particularly inositol or sucrose, a viscosity inducer and a cryoprotectant. The latter two need not be different materials to the carbohydrate. The invention is suitable for stabilizing cultures of microorganisms such as lactic acid producing strains of Lactobacillus or Streptococcus; and the cultures are useful as additives and forage, especially silage.

10 Claims, No Drawings

STABILIZED CULTURES OF
MICROORGANISMS

This is a continuation of application Ser. No. 07/862,764, filed on Sep. 29, 1992, which was abandoned upon the filing hereof.

This invention relates to stabilized cultures of microorganisms suitable for use in the presence of solid carriers in dry formulated powders and to a process for producing such stabilized cultures.

In particular the invention relates to stabilized dry cultures of Gram-negative bacteria and to a process for producing them.

Dry cultures of microorganisms have a wide and increasing range of applications. Such applications include use in silage, hay and grain additives, probiotics (as digestive aids for animals), in seed coatings, drenches and dressings, in biotransformations such as the processes described in our European Patent specifications Nos. 0076606 and 0179603 and in the manufacture of cheese and yogurt.

Of the various applications for cultures of microorganisms their use in the manufacture of cheese and yogurt has received most commercial attention to date. However a problem associated with this use has been the comparitively poor stability of the cultures of lactic acid producing bacteria employed therein when stored at room temperature. This poor stability also applies to cultures of microorganisms used for other purposes, particularly in the dry state and in the presence of solid carriers, e.g. in silage additives.

Because of poor stability for prolonged periods at room temperature cultures of lactic acid producing bacteria for use in cheese and yogurt manufacture have generally been stored and distributed under cold store conditions. In recent years however there have been improvements in the stability at room temperature of such cultures. For example a process has been described in UK Patent Specification No. 1469218 for producing stabilized dry cultures of lactic acid producing bacteria in which the following components are included in the cultures:

(a) L-ascorbic acid and/or a non-toxic, water soluble salt thereof; and (b) glutamic acid and/or aspartic acid and/or a non-toxic, water soluble salt of glutamic or aspartic acid; components (a) and (b) being included in the cultures in specified amounts.

Despite the improvements of recent years there remains a need for improved stabilized dry cultures of microorganisms, particularly for use in silage additives, which can readily be used in any physical situation. In particular there is a need for such stabilized dry cultures for use in the presence of solid carriers in dry formulated powders.

Accordingly the present invention provides a culture of a microorganism which comprises viable cells of the microorganism and stabilizing amounts of (a) an antioxidant, which is 6-deoxy-L-ascorbic, L-rhamnoascorbic, D-araboascorbic and/or ascorbic acids and/or a non-toxic, water-soluble salt of any of these acids; and (b) a monocarboxylic α-amino acid and/or a non-toxic, water soluble salt thereof.

Further the present invention provides a culture of a microorganism which comprises viable cells of the microorganism and stabilizing amounts of the following components:

(a) an antioxidant, which is 6-deoxy-L-ascorbic acid, L-rhamnoascorbic acid, D-araboascorbic acid and/or ascorbic acid and/or is a non-toxic, water soluble salt of any of these acids;

(b) An α-amino acid which is glycine, taurine, glutamic acid and/or aspartic acid and/or is a non-toxic, water soluble salt of any of these acids; and very desirably, (c) a carbohydrate;

(d) a viscosity inducer; and (e) a cryoprotectant.

The present invention further includes a method of making a dried culture of viable cells of a microorganism which comprises the steps of:

(i) cultivating viable cells of the microorganism in an aqueous nutrient containing medium at a physiological pH;

(ii) concentrating the culture produced in step (i) to a cell concentration of at least 20% w/w;

(iii) adding to the concentrated culture stabilising amounts of (a) an antioxidant which is 6-deoxy-L-ascorbic acid, L-rhamnoascorbic acid, D-arabo-ascorbic acid and/or ascorbic acid and/or is a non-toxic, water soluble salt of any of these acids; and (b) a monocarboxylic α-amino acid and/or a non-toxic, water soluble salt thereof, and causing the added components to disperse through the concentrated culture; and (iv) drying the stabilised culture.

A particular process of the present invention for producing a culture of viable cells of a microorganism comprises the steps of:

(i) cultivating viable cells of the microorganism in an aqueous nutrient containing medium at a physiological pH;

(ii) concentrating the culture produced in step (i) to a cell concentration of at least 20% w/w;

(iii) adding to the concentrated culture stabilising amounts of (a) an antioxidant which is 6-deoxy-L-ascorbic acid, L-rhamnoascorbic acid, D-arabo-ascorbic acid and/or ascorbic acid and/or is a non-toxic, water soluble salt of any of these acids; and (b) a monocarboxylic α-amino acid which is glycine, taurine, glutamic acid and/or asparaic acid and/or is a non-toxic, water soluble salt of any of these acids, and very desirably (c) a carbohydrate, (d) a viscosity inducer and (e) a cryoprotectant, and causing the added components to disperse through the concentrated culture; and (iv) drying the stabilised culture.

Suitable carbohydrates for inclusion as component (c) in the culture of the invention include sucrose, mannitol, trehalose, inositol, adonitol and combinations of two or more of these carbohydrates. Suitable viscosity inducers for inclusion as component (d) include alkyl, hydroxyalkyl and/or carboxymethyl cellulose derivatives, sodium alginate, gum Arabic, gellan gum and/or non-toxic, water soluble salts of any of these materials. Suitable cryoprotectants for inclusion as component (e) include glycopeptides and/or non-toxic, water soluble salts thereof, nonfat skimmed milk powder and/or whey powder. In this aspect of the invention the viscosity inducer and/or cryoprotectant need not be different materials from the carbohydrate. Put another way, the carbohydrate, particularly sucrose and/or inositol, can serve the function of the viscosity inducer and/or (and particularly) the cryoprotectant in this invention. However, as they can be different materials they are herein referred to separately by the terms 'viscosity inducer' and 'cryoprotectant'. When the carbohydrate serves the function of viscosity inducer and/or cryoprotectant, the amount of carbohydrate used will generally be increased in line with the amount of viscosity inducer and/or cryoprotectant it replaces. This is referred to below in the discussion on amounts of additives used.

The cultures of the invention may suitably contain a calcium source in addition to the other components (a) to (e). Suitable calcium sources include granular limestone and/or calcium hydroxide.

The cultures of the invention are highly suitable for use as dry stable cultures with high viabilities for example viabilities of the order of $10^{11}$ colony forming units per gram. They can also however be used in other physical forms for instance as frozen wet cultures.

When the culture of the invention comprises as additives an antioxidant, an α-amino acid, a carbohydrate, a viscosity inducer and a cryoprotectant it is preferred that the volume fraction of these additives in the stabilised dry culture of microorganisms is in the range 0.39 to 0.63, particularly in the range 0.45 to 0.48. The volume fraction range corresponds approximately to a mass fraction range of 0.25 to 0.45, particularly 0.3 to 0.32.

The mass fractions of the individual additives in a stabilised dry culture of microorganisms comprising as additives an antioxidant, an α-amino acid, and, when present, a carbohydrate, a viscosity inducer and a cryoprotectant are preferably in the following ranges:

(a) antioxidant—0.05 to 0.3, particularly 0.25 to 0.3;

(b) α-amino acid—0.05 to 0.3, particularly 0.25 to 0.3 being suitably equal to that of the antioxidant (a) above;

(c) carbohydrate—0.005 to 0.2, e.g. up to 0.14, particularly approximately 0.05;

(d) viscosity inducer—0.005 to 0.14, particularly approximately 0.02;

(e) cryprotectant—0.2 to 0.4 of the mass of the cells to be protected typically corresponding to a mass fraction of about 0.1 to 0.2 (based on the culture).

When the carbohydrate acts as the viscosity inducer and/or cryoprotectant, the additional amount of carbohydrate used will generally be approximately equal to the viscosity inducer and/or cryoprotectant it replaces within the ranges set out above. Thus, when the carbohydrate acts also as the cryoprotectant the amount used will typically be in the (mass fraction) range 0.15 to 0.4 particularly 0.2 to 0.3, and when it acts also as both the cryoprotectant and and viscosity inducer, the amount used will typically be in the range 0.2 to 0.5 particularly 0.25 to 0.4

When a calcium source is included this is suitably present in an amount in the range 0.001 to 0.01, preferably approximately 0.05 being a mass fraction of the calcium source in the stabilised dry culture of microorganisms and additives (i.e. as defined above for the other additives).

When the culture of the invention is a culture of a microorganism which is sensitive to freezing and/or thawing it is preferred that the total weight percentage of solutes in the supernatant liquid is increased to a value in the range 50% to 70% by the addition of the cryoprotectant and viscosity inducer (or further carbohydrate when it serves these functions) particularly in the proportions 1:0.2 respectively.

The inclusion of the carbohydrate, especially sucrose and/or inositol, seems to have the effect, in a dried culture, of providing a glass or plastic like envelope for the microorganisms. At temperatures below the glass transition temperature of the carbohydrate (in the dried culture), it increases the resistance to deterioration of the of the culture. We believe, but do not know for certain, that the carbohydrate reduces the ingress of moisture. A practical advantage is that carbohydrate containing dried cultures can be mixed with carriers or diluents which themselves contain significant proportions of bonded water.

In the process of the invention a microorganism is cultivated in step (i) in a suitable nutrient medium under appropriate conditions of, e.g. temperature and pH. The pH should be an appropriate physiological pH for the microorganism under cultivation. In the case of Lactobacillus strains this will be a value in the range pH 6.2 to 6.8. Cultivation may be in batch or continuous culture, continuous cultivation being preferred. Culture produced during step (i) is then concentrated during step (ii) by any suitable means, for example by centrifugation or by ultrafiltration in order to reach the cell concentration required. After concentration in step (ii) the additives may be added to the concentrated culture during step (iii) in any suitable manner and may be mixed into the culture by any suitable means in order to achieve a satisfactory degree of dispersion throughout it. If, after the addition of the additives and their dispersion through the culture, the pH of the concentrated culture is found to have fallen outside the appropriate physiological range (6.2 to 6.8 in the case of Lactobacillus strains) the action should be taken to return the pH to a value within this range. In step (iv) of the process it is preferred that the stabilised culture is freeze dried, cryogenically or otherwise. When freeze drying is employed it is desirable that the culture is frozen in a manner such that a frozen product with a surface area to volume ratio in the range 3 to 0.4 $mm^{-1}$ is formed, representing spheres or cylinders in the diameter range 2 to 15 mm respectively. Preferably when freeze drying is used in step (iv) the stabilised culture is dried over a period of 12 to 48 hours. The stabilised dry culture is also preferably annealed for a period of approximately 12 hours at a temperature in the range 30° to 40° C., but possibly as high as 60° C. In the drying step (iv) it is preferred that the moisture content of the stabilised culture is reduced to a value not exceeding 5% by weight.

Particularly conveniently, the stabilised culture of the invention can be made by freeze drying in the form of "prills". Prills are relatively porous solid roughly spherical, cylindrical or vermiform particles. In this invention, they can be made by rapidly freezing approximately spherical droplets or a roughly cylindrical stream of the aqueous culture of the microorganisms containing the stabilizer additives and subsequently drying the particles by subliming off water (now frozen as ice) under vacuum. Conveniently, the rapid freezing can be carried out by dispersing the aqueous culture as droplets, particles or a thin stream and then contacting them with a medium at a suitably low temperature e.g. one cooled to liquid nitrogen temperatures. The mechanical form of the aqueous culture, at this stage, will depend on its solid content and, thus, its viscosity, which can range from a mobile liquid to a pasty dispersion. The cooling medium can be liquid nitrogen itself, but the gaseous nitrogen which boils off during cooling tends to insulate the material being cooled thus slowing the freezing process. For this reason, it is usually better that the cooling medium is not itself liquid nitrogen but is a material cooled to liquid nitrogen temperatures. Suitably, it can be an inert non-toxic liquid (at liquid nitrogen temperatures) which boils at somewhat higher temperatures, or it can be a solid surface cooled by evaporation of liquid nitrogen. Where the aqueous culture is a pasty dispersion, it is especially convenient to use a chilled metal e.g. stainless steel, drum as the cooling medium and extrude the dispersion onto it to freeze it as short cylinders or short vermiform particles.

The prills are typically dried by heating under vacuum to sublime off the water ice. Plainly it is desirable to do this as rapidly as possible and this implies relatively high temperatures. Equally, during drying the frozen culture (as prills or in other form) should not be heated to a temperature that would damage it. In this invention the culture should be kept at a temperature sufficiently low that the water ice does not melt and, when the stabilizing additives include a carbohydrate, below the glass transition temperature of the carbohydrate (in the presence of the ice). This maximum temperature rises with decreasing water content so that, as drying proceeds the temperature of the culture can be allowed to rise, thus speeding subsequent drying. The appropriate temperature (of the culture) time profile will also depend on drying equipment design but we expect that the skilled man, experienced in using the equipment available to him, will not have serious difficulty in establishing a suitable profile to achieve satisfactory drying. Typically, we have found that suitable culture temperatures for drying are, at the start from −30° to −40° C. and, towards the end of drying, from 30 to 50 and possibly up to 60° C. By holding the temperature for a period at the end of drying the freeze dried culture can be annealed without requiring a specific separate annealing step. Of course, the medium used to heat the culture during drying will be at a higher temperature than the culture itself, which is cooled by the sublimation.

The dried stabilised microorganisms can typically remain viable at temperatures up to about 60° C. (although storage stability at such temperatures will probably be reduced). At temperatures above about 65° C. they become progressively inactivated or killed and significant exposure above 75° C. is likely to be fatal to the microorganism.

The culture of the invention may be a culture of any microorganism. Preferably however it is a culture of a Gram-negative bacterium and in particular a culture of such a bacterium useful as the active ingredient in a silage additive.

Silage is produced by the fermentation of crops such as grasses, cereal grains e.g. maize, wheat, barley and sorghum, legumes e.g. clovers, peas and lucerne, and rice. In its simplest form the fermentation is a natural fermentation brought about by native lactic acid producing bacteria present on the crop when it is harvested. The fermentation can however be improved by the addition of silage additives containing selected lactic acid producing bacteria to the crop. Use of such silage additives results in improved preservation and increased stability of the silage product with reduced in-silo losses and improved performance from animals fed on the product. Silage additives containing bacteria can be applied to harvested crops either as liquid suspensions of bacteria applied using suitable applicators or as solid compositions comprising bacteria mixed with carriers. Bacteria suitable for use in silage additives include any lactic acid producing strains of Lactobacillus or Streptococcus suitable for making silage. Suitable strains include strains of the species *Lactobacillus amylophilus, Lactobacillus caseii, Lactobacillus plantarum, Lactobacillus acidophilus, Lactobacillus curvatus, Lactobacillus brevis, Streptococcus lactis, Streptococcus thermophilus, Streptococcus faecium* and *Streptococcus faecalis*. The strain *Lactobacillus plantarum* has been deposited under the terms of the Budapest Treaty and was deposited with the National Collections of Industrial and Marine Bacteria Ltd. on Nov. 12, 1986, Strain number—MTD/1, under Accession Number NCIB 40027. Suitable carriers that can be used include dry or anhydrous materials such as cenospheres or glass beads e.g. ballotini, or where the dried culture has enhanced moisture resistance by including a carbohydrate, materials such as limestone or maize grits which have a bound water content of up to several percent. Carriers with elevated water content, particularly if in unbound form can be dried e.g. using desicants such as zeolites or silicas. If used undried it is probable that this will reduce the storage stability of the culture.

In addition to their use in silage additives, the cultures of the invention can be used in a wide variety of other applications. They can be used in hay and grain additives, probiotics (as digestive acids for animals), in seed coatings, drenches and dressings, biotransformations such as the processes described in European Patent Specifications Nos. 0076606 and 0179603 and in the manufacture of yogurt and cheese.

The cultures to which the invention is applied comprise microorganisms which are compacted together in a manner analogous to a bed of packed cylinders. Such a bed will typically contain a voidage fraction of about 40% by volume which is generally filled by air and which we believe contributes to instability in the dry cultures. In the cultures of the invention the additives collectively wholly or partially fill the voidage space between microorganisms and exclude air therefrom. This, according to our hypothesis, reduces the source of instability and contributes to the efficacy of the cultures of the invention.

The invention is illustrated by the following Examples. All parts and percentages are by weight unless otherwise stated.

EXAMPLE 1

*Lactobacillus plantarum* strain MTD/1 (NCIMB 40027, a culture of which was deposited for patent purposes under the terms of the Budapest Treaty at the National Collections of Industrial & Marine Bacteria (NCIMB) PO Box 31, 135 Abbey Road, Aberdeen, AB9 8DG, UK on 20 July 1988) was grown continuously and concentrated to 20% w/w by centrifugation.

With the concentrate was mixed 50 g/kg non-fat skimmed milk powder, 120 g/kg sodium ascorbate, 125 g/kg glycine, and 25 g/kg limestone.

The product was frozen into prills by immersing droplets of the culture in liquid nitrogen. The frozen prills were dried by freeze drying over a period of 36 hours ending the drying cycle at 40° C. to a water content of 2 to 3% w/w.

Samples of product were stored at 37°±3° C. and viability was monitored over a period of 3 months to give the following results.

| TIME (Days) | VIABILITY (Colony Forming Units/g) |
| --- | --- |
| 0 | 3E11* |
| 1 | 3E11 |
| 2 | 3E11 |
| 10 | 2E11 |
| 14 | 2E11 |
| 18 | 1E11 |
| 23 | 2E11 |
| 28 | 2E11 |
| 32 | 2E11 |
| 61 | 1E11 |
| 70 | 1E11 |

*3E11 = $3 \times 10^{11}$ etc.

A blank, without additives, showed a decade drop in viability over 14 days at 37° C.

EXAMPLE 2

A culture of *L. plantarum* strain MTD/1 was grown and harvested as described in Example 1. The following additives were mixed into cell concentrate: 50 g/kg non-fat skimmed milk powder, 70 g/kg sodium ascorbate, 70 g/kg glycine, 25 g/kg limestone, 250 g/kg sucrose. The resulting mixture was frozen and dried as described in Example 1. Samples of the dried product were ground to a powder and diluted a hundredfold with granular limestone as a carrier. Samples were monitored over a period of 36 days at 37°±3° C. to give the following results:

| TIME (Days) | VIABILITY (Colony Forming Units/g) |
| --- | --- |
| 0 | 3E9 |
| 15 | 2E9 |
| 36 | 1E9 |

EXAMPLE 3

A culture of *L. plantarum* strain MTD/1 was grown, harvested and processed as described in Example 1, but with the following additives: 50 g/kg non-fat skimmed milk powder, 120 g/kg sodium erythrobate, 120 g/kg glycine, 25 g/kg sucrose, 6 g/kg carboxymethylcellulose, 215 g/kg limestone.

The dry product was ground to a powder; one sample was stored at 37°±3° C. the other diluted a hundredfold with granular limestone carrier and stored at 37°±3° C. Viabilities over the period of storage are as follows.

| | VIABILITY (Colony Forming Units/g) | |
| --- | --- | --- |
| TIME (Days) | with carrier | pure |
| 0 | 6E9 | 3E11 |
| 14 | 2E9 | 2E11 |

A blank sample with carrier typically shows two decades loss of viability over 14 days at 37° C.

EXAMPLE 4

A culture of *L. plantarum* strain MTD/1 was grown and harvested as described in Example 1. The following additives were mixed into the cell concentrate: 120 g/kg glycine, 120 g/kg sodium erythrobate (a commercially available sodium salt of D-araboascorbic acid—which is sometimes known as iso-ascorbic acid), 250 g/kg sucrose.

The resulting mixture was frozen using a 'Cryostream' (Air Products Ltd) liquid nitrogen cooled drum freezing plant and the resulting prills were freeze dried at a shelf temperature of 50° C. over 41 hours at a pressure of less than 0.4 mbar so that the temperature of the prills did not use above the glass transition temperature of the carbohydrate (sucrose).

Samples of dried product which had a moisture content of 4.8% were ground to a powder and split into two portions (A and B). One portion (A) was diluted a hundred fold with granular limestone as a carrier. Both samples were monitored over a period of 14 days at 37°±3° C. to give the following results:

| | VIABILITY (Colony Forming Units/g) | |
| --- | --- | --- |
| TIME (Days) | A | B |
| 0 | 1.6E9 | 1.5E11 |
| 14 | 1.8E9 | 1.4E11 |

EXAMPLE 5

A culture of *L. plantarum* strain MTD/1 was grown and harvested as described in Example 1. The following additives were mixed into the cell concentrate: 60 g/kg glycine, 60 g/kg sodium erythrobate and 250 g/kg sucrose.

The mixture was then processed as described in Example 4 but was dried at a shelf temperature of 50° C. over 12 hours at a pressure of less than 0.4 mbar. The product had a moisture content of 3.9%. Samples were monitored over a period of 14 days at 37°±3° C. to give the following results:

| | VIABILITY (Colony Forming Units/g) | |
| --- | --- | --- |
| TIME (Days) | A | B |
| 0 | 1.0E9 | 2E11 |
| 14 | 1.0E9 | 1.3E11 |

EXAMPLE 6

A sample of *L. plantarum* strain MTD/1 was grown, harvested, formulated and processed as in Example 5 but was dried at a shelf temperature of 50° C. over 41 hours at a pressure of less than 0.4 mbar. The product had a moisture content of 5.7%. Samples were monitored over a period of 14 days at 37°±3° C. to give the following results:

| | VIABILITY (Colony Forming Units/g) | |
| --- | --- | --- |
| TIME (Days) | A | B |
| 0 | 1.8E9 | 2.4E11 |
| 14 | 2.5E9 | 2.1E11 |

I claim:

1. A particulate dry culture comprising:
   viable microorganism cells;
   antioxidant selected from the group consisting of ascorbate, 6-deoxy-L-ascorbate, D-araboascorbate and L-rhamnoascorbate and present at a mass fraction of 0.05 to 0.3;
   α-amino-carboxylate selected from the group consisting of α-amino monocarboxylate, glutamate and aspartate and present at a mass fraction of 0.05 to 0.3; and
   carbohydrate present at a mass fraction of 0.2 to 0.5;
   said antioxidant and said amino-carboxylate being present in an amount sufficient to stabilize said dry culture, and said carbohydrate forming an envelope for the microorganism cells, limiting ingress of moisture.

2. A dry culture according to claim 1 in which the carbohydrate is selected from the group consisting of non-fat skimmed milk powder and sucrose.

3. A particulate dry culture comprising:

viable microorganism cells;

antioxidant selected from the group consisting of ascorbate, 6-deoxy-L-ascorbate, D-araboascorbate and L-rhamnoascorbate;

α-amino-carboxylate selected from the group consisting of α-amino monocarboxylate, glutamate and aspartate; and carbohydrate;

in which the quantities by weight per 100 parts by weight of the microorganism cells are:

antioxidant 30–60;

aminocarboxylate 30–62.5;

carbohydrate 25–125.

4. A dry culture according to claim 1 in which the carbohydrate constitutes 25 to 45 weight percent of said dry culture.

5. A dry culture according to claim 1 in the form of prills, said prills being obtained by drying spheres or cylinders which are in the diameter range 2–15 mm before drying.

6. A dry culture according to claim 1 further comprising carboxymethyl cellulose.

7. A dry culture according to claim 1 further comprising calcium carbonate at 12.5 to 107.5 parts by weight per 100 parts of the microorganism cells by weight.

8. A dry culture according to claim 1 in which the microorganism is a lactic acid producing bacterium.

9. A dry culture according to claim 8 in which the antioxidant is D-araboascorbate and the α-amino-carboxylate is glycinate.

10. A diluted composition comprising a dry culture according to claim 1 and 100 parts of granular limestone per part of said dry culture by weight.

* * * * *